US00PP30588P2

(12) United States Plant Patent
Kordes

(10) Patent No.: US PP30,588 P2
(45) Date of Patent: Jun. 25, 2019

(54) CLIMBING ROSE PLANT NAMED 'KORTANGENU'

(50) Latin Name: *Rosa hybrida*
Varietal Denomination: KORtangenu

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE ROSENSCHULEN GMBH & CO KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/732,546

(22) Filed: Nov. 27, 2017

(51) Int. Cl.
*A01H 5/02* (2018.01)
*A01H 6/74* (2018.01)

(52) U.S. Cl.
USPC ..... Plt./112
CPC ..... *A01H 6/749* (2018.05)

(58) Field of Classification Search
USPC ..... Plt./112
See application file for complete search history.

(56) References Cited

U.S. PATENT DOCUMENTS

PP4,596 P * 9/1980 Moore ..... Plt./4

* cited by examiner

*Primary Examiner* — Annette H Para
(74) *Attorney, Agent, or Firm* — Buchanan Ingersoll & Rooney PC

(57) ABSTRACT

A new and distinct variety of Climbing Rose Plant, herein referred to by its cultivar name, 'KORtangenu', is provided which forms in abundance on a substantially continuous basis attractive, orange-yellow colored blossoms. The vegetation is vigorous and the growth habit is climbing. Attractive, glossy, dark green foliage is formed. The resistance to disease is very good. The new variety is particularly well suited for providing distinctive ornamentation in the landscape.

2 Drawing Sheets

Figure 1:
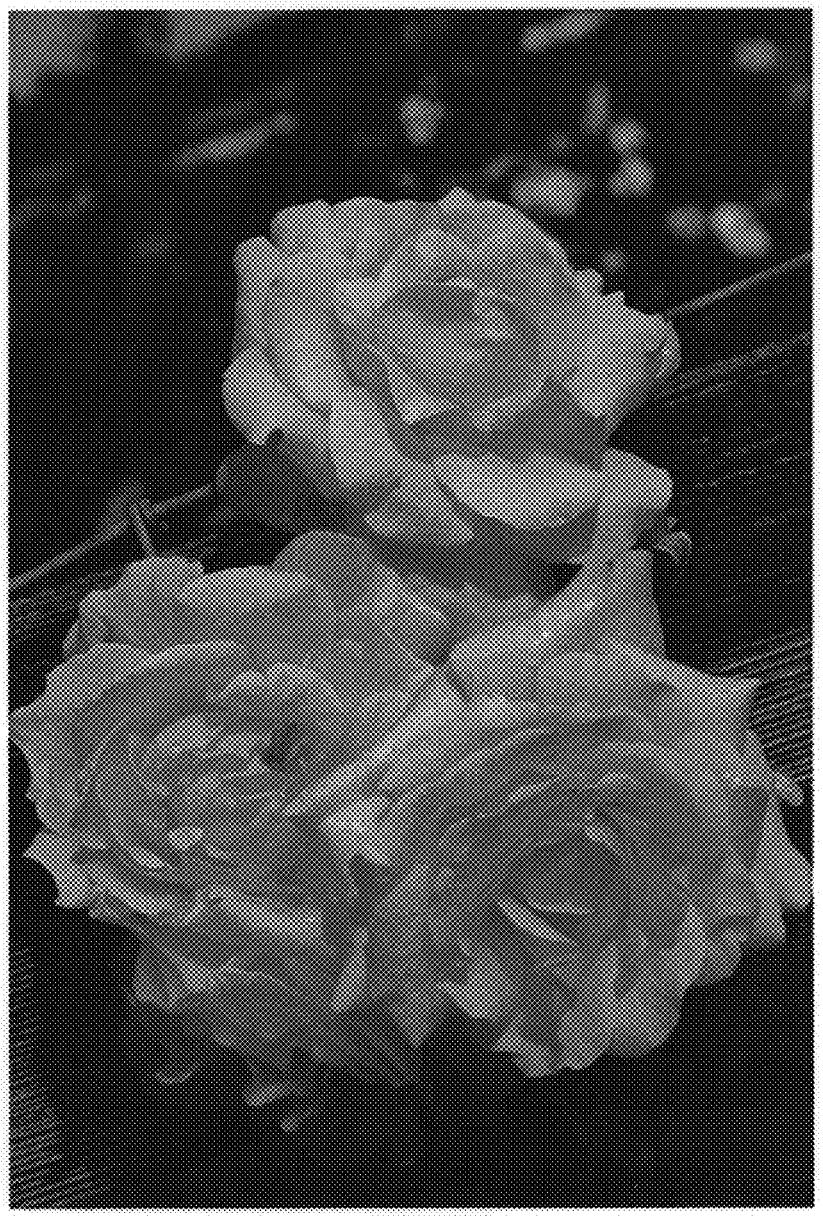

Botanical/commercial classification:
Latin name—*Rosa hybrida.*
Common name—Climbing Rose Plant.
Varietal denomination: 'KORtangenu'.

SUMMARY OF THE INVENTION

The new variety of *Rosa hybrida* Climbing Rose Plant of the present invention was created during 2002 at Offenseth-Sparrieshoop, Germany by artificial pollination wherein two parents were crossed which previously had been studied in the hope that they would contribute the desired characteristics. The female parent (i.e., seed parent) of the new variety was the 'INTERflocu' variety (non-patented in the United States). The male parent (i.e., pollen parent) was the 'Johannes Rau' variety (non-patented in the United States).

The parentage can be summarized as follows:

'INTERflocu' x 'Johannes Rau'

The seeds resulting from the above pollination were sown and small plants were obtained which were physically and biologically different from each other. Selective study resulted in the identification of a single plant of the new variety.

It was found that the new Climbing Rose Plant of the present invention possesses the following combination of characteristics:

(a) abundantly and substantially continuously forms attractive, orange-yellow colored blossoms,
(b) exhibits a climbing growth habit,
(c) forms vigorous vegetation, (d) forms attractive ornamental glossy, dark green foliage, and
(e) exhibits very good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'INTERflocu' variety (i.e., seed parent) displays a cupped shaped flower which is cream yellow with pink edges in color, whereas the new variety displays a pointed shaped flower which is orange-yellow in color and has more vigor than the 'INTERflocu' variety. Additionally, the 'Johannes Rau' variety (i.e., pollen parent) exhibits yellow colored blossoms, whereas the new variety displays orange-yellow colored blossoms and has a smaller petal count than the 'Johannes Rau' variety. Moreover, the new variety can be readily distinguished from non-parental related similar varieties. For example, the 'Orange Cascade' variety (U.S. Plant Pat. No. 4,596) exhibits smaller flowers compared to the new variety and produces about 45 petals, whereas the new variety produces approximately 25 petals on average. Additionally, the 'Joseph's Coat' variety exhibits smaller flower size than that of the new variety and displays a blend of yellow, red, and orange colored flowers, whereas the new variety displays orange-yellow colored flowers.

The new variety has been found to undergo asexual propagation in Klein Offenseth-Sparrieshoop, Germany by a number of routes such as budding. Asexual propagation techniques in Germany have shown that the characteristics of the new variety are homogeneous, stable, and strictly transmissible by such asexual propagation from one generation to another. Accordingly, the new variety undergoes asexual propagation in a true-to-type manner.

The new variety has been named 'KORtangenu'.

BRIEF DESCRIPTION OF THE PHOTOGRAPHS

The accompanying photograph shows, as nearly true as it is reasonably possible to make the same in color illustrations of this character, typical specimens of the new variety. The illustrated rose plant of the new variety was approximately three years of age and was observed at Jacksonville, Oreg. during October 2011 while growing outdoors on understock.

FIG. 1—illustrates specimens of flowers in the course of opening.

Figure 2:
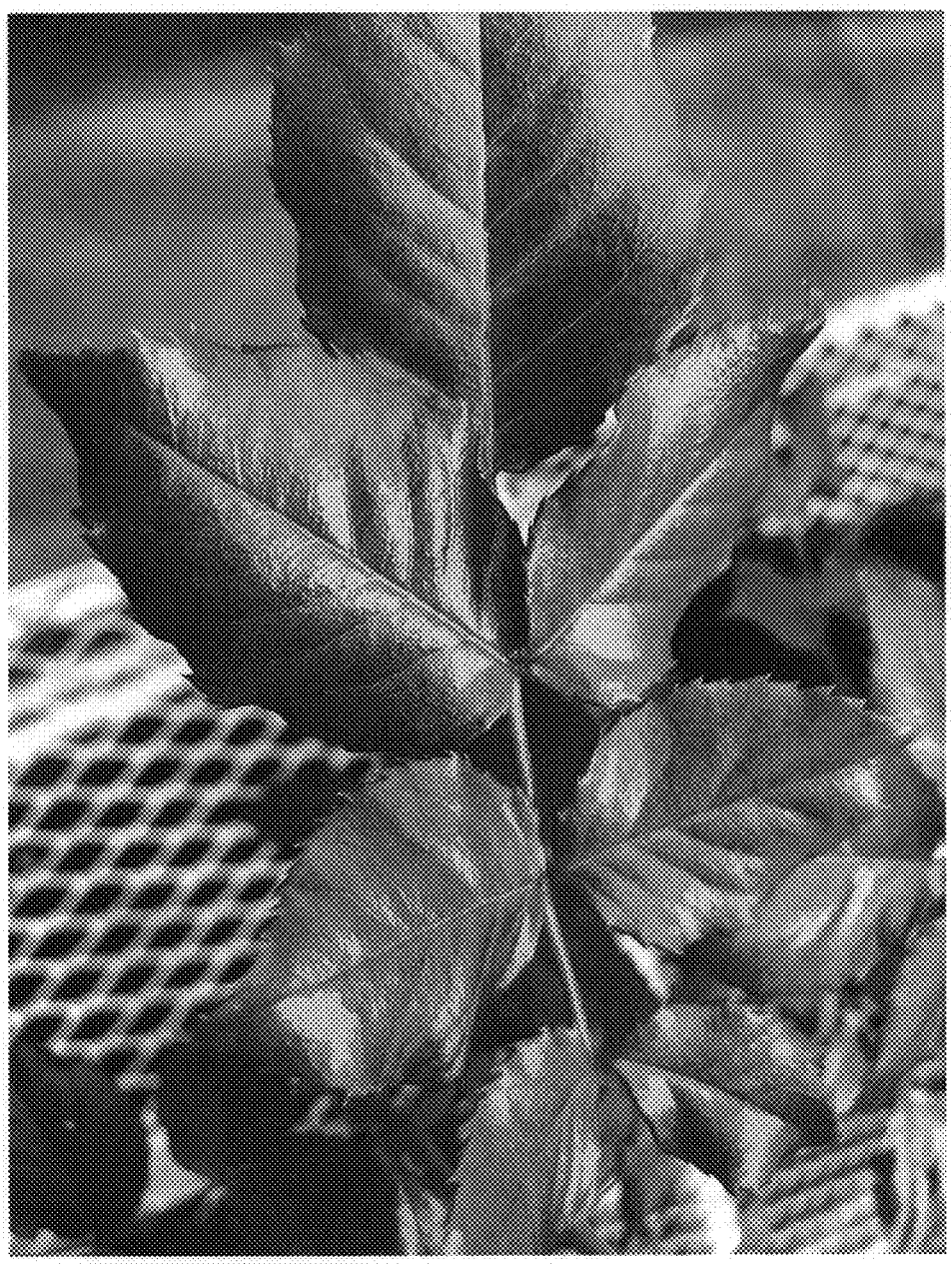

FIG. 2—illustrates specimen of the foliage—plane view—obverse.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a two-year-old specimen of the new variety, observed during February, while growing in a one-gallon container on its own roots in a greenhouse at Cochranville, Pa.

Class: Climbing Rose Plant.

Plant:

*Habit*.—Climbing, very bushy and upright.

*Height*.—Approximately 60.0 cm on average from the soil plane in a one gallon container.

*Width*.—Approximately 40.0 cm on average in a one gallon container.

Branches:

*Stem color*.—Old wood: commonly near Yellow-Green Group 148A. Young stems: commonly near Yellow-Green Group 144A.

*Main stem length*.—Approximately 60.0 cm on average.

*Secondary stem length*.—Approximately 25.0 cm on average.

*Surface texture*.—Mature stems are smooth to rough where the wood is becoming harder; immature stems are smooth.

*Thorns*.—Number: approximately 6 thorns per 5.0 cm of stem length, on average. Young thorns: length is approximately 6.0 mm on average, width is approximately 2.0 mm at point of attachment on average, and color is commonly near Yellow-Green Group 144A. Old thorns: length is approximately 6.0 mm on average, width is approximately 2.0 mm at point of attachment on average, and color is commonly near Greyed-Orange Group 177D.

Foliage:

*General appearance*.—Glossy, dark green.

*Young foliage*.—Upper surface color: commonly near Green Group 137B. Under surface color: commonly near Green Group 137C.

*Old foliage*.—Upper surface color: commonly near Green Group 137A. Under surface color: commonly near Green Group 137B.

*Petiole*.—Upper surface: texture is smooth; color is commonly near Green Group 143C. Under surface: texture is smooth, color is commonly near Green Group 143C.

*Rachis*.—Color: upper surface is commonly near Green Group 143B with some highlights of near Greyed-Red Group 182A, under surface is commonly near Green Group 143B. Size: length is approximately 6.0 cm on average. Surface texture: smooth.

*Stipules*.—Length: approximately 1.0 cm on average. Width: approximately 9.0 mm on average. Margin: entire to erose. Color: upper surface is commonly near Yellow-Green Group 144A; under surface is commonly near Yellow-Green Group 144A.

*Leaf margin*.—Serrate.

*Glossiness of upper side of leaf*.—Very glossy.

*Leaf arrangement*.—Odd pinnate.

Leaflets:

*Number*.—3, 5, and 7.

*Shape*.—Ovate.

*Venation*.—Pattern is reticulate; upper surface color is commonly near Green Group 137C; and lower surface color is commonly near Green Group 137D.

*Texture*.—Upper surface is smooth; under surface is smooth.

*Size*.—Terminal leaflet: length is approximately 4.5 cm on average; width is approximately 3.0 cm on average; apex is acute; and base is rounded. Lower leaflets: length is approximately 3.4 cm on average and width is approximately 2.3 cm on average. 5-Leaflet leaf: length is approximately 9.5 cm on average and width is approximately 7.0 cm on average.

*Terminal leaflet general*.—Glossiness intensity of upper surface is strong; margin undulation is moderate; apex shape is acute; base shape is rounded.

Inflorescence:

*Number of blooms per stem or in a cluster*.—Commonly between 1 and 5 blooms per stem on average.

*Peduncle*.—Color: commonly Yellow-Green Group 144A. Diameter: approximately 3.0 mm on average. Length: approximately 5.0 cm on average. Surface texture: sparely covered in short, flexible thorns that measure less than 1.0 mm in length.

*Sepals*.—Number commonly 5. Upper surface color and texture: covered in short pubescence and color is commonly near Yellow-Green Group 144A. Under surface color and texture: puberulent and color is commonly near Yellow-Green Group 144B. Size: length is approximately 3.0 cm on average and width is approximately 7.0 mm on average. Shape: lanceolate; apex is aristate. Margin: entire with occasional extensions on two or three sepals measuring approximately 5.0 mm to 1.0 cm in length and approximately 5.0 mm in width.

*Bud*.—Shape: ovoid. Size: length is approximately 3.0 cm on average; width is approximately 2.0 cm on average. Color (when opening): commonly near Orange-Red Group N34B.

*Flower*.—Orange-yellow colored. Shape: round, pointed. Form: double, traditional. Diameter: approximately 9.0 cm on average. Height: approximately 6.0 cm on average. Color upper and under surfaces when fully open: commonly near Yellow-Orange Group 14B at the point of attachment and blending to near Yellow-Orange Group 20A surrounding the central portion of the petal and near Orange Group 29B towards the margins.

*Fragrance*.—Very light sweet fragrance.

*Petal*.—Number: approximately 25 on average. Drop: good. Length: inner petals are approximately 3.0 cm on average; outer petals are approximately 6.0 cm on average. Width: inner petals are approximately 3.5 cm on average; outer petals are approximately 5.5 cm on average. Shape: overall shape is broadly obovate; apex is rounded; and base is rounded. Margin: entire. Margin undulation: moderate.

*Petaloids*.—Not produced.

*Basal spot*.—Not produced.

*Stamen*.—Number: approximately 112 on average. Anthers: number is about 112 and color is commonly near Yellow-Orange Group 17B; length is approximately 3.0 mm on average. Filaments: length is approximately 1.0 cm on average and color is commonly near Yellow-Orange Group 21A at the point of attachment, mostly near Orange-Red Group 32A.

*Pistils*.—Arrangement: separate and free. Number: approximately 75. Style: color is commonly near Yellow Group 4C; length is approximately 8.0 mm on average. Stigma: color is commonly near Yellow Group 5A; diameter is commonly less than 1.0 mm on average.

*Receptacle*.—Achenes stand on the bottom and wall; diameter is approximately 1.3 cm on average, shape is round, color is commonly near Yellow-Green Group 144A, and surface texture is smooth.

*Pollen*.—None observed.

*Hips/seed*.—None observed.

Development:

*Vegetation*.—Dark green, vigorous, and strong; the amount of vegetative growth per season observed while in containers at Cochranville, Pa. is approximately 45.0 to 60.0 cm on average.

*Blooming*.—Abundant and substantially continuous from spring through frost.

*Hardiness*.—Hardy to USDA Zone 5.

*Tolerance to diseases*.—Very good resistance for *Sphaerotheca pannosa* mildew.

Plants of the 'KORtangenu' variety have not been observed under all possible environmental conditions to date. Accordingly, it is possible that the phenotypic expression may vary somewhat with changes in light intensity and duration, cultural practices, and other environmental conditions.

I claim:

1. A new and distinct Climbing Rose Plant characterized by the following combination of characteristics:

(a) abundantly and substantially continuously forms attractive, orange-yellow colored blossoms, (b) exhibits a climbing habit, (c) forms vigorous vegetation, (d) forms attractive ornamental glossy, dark green foliage, and (e) exhibits very good disease resistance;

substantially as herein shown and described.

* * * * *